(12) United States Patent
Elkins

(10) Patent No.: US 7,186,270 B2
(45) Date of Patent: Mar. 6, 2007

(54) FOOT-OPERATED CONTROLLER

(75) Inventor: Jeffrey L. Elkins, Rockford, MI (US)

(73) Assignee: Jeffrey Elkins 2002 Corporate Trust, Grand Rapids, MI (US)

( * ) Notice: Subject to any disclaimer, the term of this patent is extended or adjusted under 35 U.S.C. 154(b) by 232 days.

(21) Appl. No.: 10/685,978

(22) Filed: Oct. 15, 2003

(65) Prior Publication Data

US 2004/0078091 A1   Apr. 22, 2004

Related U.S. Application Data

(60) Provisional application No. 60/418,508, filed on Oct. 15, 2002.

(51) Int. Cl.
*A61F 2/48* (2006.01)
*A61F 2/70* (2006.01)
*H01H 3/14* (2006.01)

(52) U.S. Cl. .......................... 623/24; 200/86.5; 623/57

(58) Field of Classification Search ................. 623/24, 623/25, 57, 61, 62, 63, 64; 200/86.5
See application file for complete search history.

(56) References Cited

U.S. PATENT DOCUMENTS

| | | | |
|---|---|---|---|
| 1,305,169 A | 5/1919 | Rohrmann | |
| 1,484,913 A | 2/1924 | Surry | |
| 2,422,302 A | 6/1947 | Horn | |
| 2,640,994 A * | 6/1953 | Alderson | 623/24 |
| 3,345,647 A | 10/1967 | Gentiluomo | |
| 4,685,929 A | 8/1987 | Monestier | |
| 4,734,034 A | 3/1988 | Maness et al. | |
| 4,770,662 A | 9/1988 | Giampapa | |
| 4,834,761 A | 5/1989 | Walters | |
| 4,856,993 A | 8/1989 | Maness et al. | |
| 4,865,613 A | 9/1989 | Rizzo | |
| 5,021,617 A | 6/1991 | DeShong | |
| 5,033,291 A | 7/1991 | Podoloff et al. | |
| 5,062,855 A | 11/1991 | Rincoe | |
| 5,071,114 A * | 12/1991 | Persaud et al. | 472/70 |
| 5,080,682 A | 1/1992 | Schectman | |
| 5,086,652 A | 2/1992 | Kropp | |
| 5,246,463 A | 9/1993 | Giampapa | |
| 5,323,650 A * | 6/1994 | Fullen et al. | 73/172 |
| 5,340,953 A * | 8/1994 | Krebs et al. | 200/86.5 |
| 5,413,611 A | 5/1995 | Haslam, II et al. | |

(Continued)

FOREIGN PATENT DOCUMENTS

DE    10038446 A1 *   2/2002

(Continued)

*Primary Examiner*—Corrine McDermott
*Assistant Examiner*—Thomas J. Sweet
(74) *Attorney, Agent, or Firm*—Price, Heneveld, Cooper, DeWitt, & Litton, LLP

(57) ABSTRACT

A practical control device having up to eight independent channels of communication for simultaneously operating a plurality of electromechanical devices or for simultaneously performing a plurality of independent functions on an electromechanical device, such as a prosthetic hand, includes a foot-operated controller and a microprocessor. The foot-controller includes a plurality of pressure sensors mounted at selected locations on a substrate. The microprocessor converts sensor inputs from the foot-operated controller into commands for a controllable electromechanical device such as a prosthetic hand. Commands may be communicated via a radio transmitter or via hard-wiring.

7 Claims, 4 Drawing Sheets

U.S. PATENT DOCUMENTS

| | | | |
|---|---|---|---|
| 5,437,289 A * | 8/1995 | Liverance et al. | 600/592 |
| 5,471,405 A * | 11/1995 | Marsh | 702/41 |
| 5,505,072 A | 4/1996 | Oreper | |
| 5,756,904 A | 5/1998 | Oreper et al. | |
| 5,813,142 A * | 9/1998 | Demon | 36/29 |
| 5,893,891 A * | 4/1999 | Zahedi | 623/24 |
| 5,905,209 A | 5/1999 | Oreper | |
| 5,941,835 A * | 8/1999 | Sundman | 600/592 |
| 5,941,914 A | 8/1999 | Jacobsen et al. | |
| 6,024,575 A * | 2/2000 | Ulrich | 434/236 |
| 6,032,542 A | 3/2000 | Warnick et al. | |
| 6,195,921 B1 * | 3/2001 | Truong | 36/136 |
| 6,225,814 B1 | 5/2001 | Oreper et al. | |
| 6,272,936 B1 | 8/2001 | Oreper et al. | |
| 6,423,098 B1 * | 7/2002 | Biedermann | 623/24 |
| 6,679,920 B2 * | 1/2004 | Biedermann et al. | 623/24 |
| 6,740,123 B2 * | 5/2004 | Davalli et al. | 623/24 |
| 6,770,045 B2 * | 8/2004 | Naft et al. | 602/16 |
| 6,836,744 B1 * | 12/2004 | Asphahani et al. | 702/141 |
| 6,964,205 B2 | 11/2005 | Papakostas et al. | |
| 2002/0089506 A1 * | 7/2002 | Templeman | 345/473 |
| 2002/0167486 A1 | 11/2002 | Tan et al. | |
| 2003/0009308 A1 | 1/2003 | Kirtley | |
| 2003/0196352 A1 * | 10/2003 | Bledsoe et al. | 36/110 |
| 2003/0209132 A1 * | 11/2003 | Mishima | 84/730 |
| 2004/0049290 A1 * | 3/2004 | Bedard | 623/24 |
| 2004/0088057 A1 * | 5/2004 | Bedard | 623/25 |
| 2005/0145045 A1 | 7/2005 | Papakostas et al. | |
| 2005/0268699 A1 | 12/2005 | Papakostas et al. | |

FOREIGN PATENT DOCUMENTS

WO  WO 200135818 A2 *  5/2001

* cited by examiner

FOOT-OPERATED CONTROLLER

CROSS-REFERENCE TO RELATED APPLICATION

This application claims priority under 35 U.S.C. § 119(e) on U.S. Provisional Application No. 60/418,508 entitled FOOT-OPERATED CONTROLLER, filed Oct. 15, 2002, by Jeffrey L. Elkins, the entire disclosure of which is incorporated herein by reference.

FIELD OF THE INVENTION

This invention relates to foot-operated controllers, and more particularly to foot-operated controllers for generating a plurality of independent signals.

BACKGROUND OF THE INVENTION

Foot-operated controllers have traditionally been limited to pedals mechanically linked to valves, levers, regulators or the like, such as accelerator and brake pedals for automobiles, or pedals capable of generating only a single electrical signal, such as for controlling a sewing machine. These conventional foot-operated controllers are not practical for simultaneously controlling multiple functions in a more complicated device such as a prosthetic hand.

Annually, approximately 40,000 people in the United States either lose or are born without a limb. Approximately 12,000 of these cases involve an upper extremity. There are three general categories of upper extremity prosthesis. These include a passive, cosmetic prosthesis; a cable-driven body-powered prosthesis; and an externally powered prosthesis that is electrically controlled by either myoelectric sensors or specialized switches.

The cable-driven, body-powered, upper-limb prostheses have not changed significantly since development in the 1950s. These prostheses employ relatively old technology involving the use of a shoulder harness and steel cables for operation. The externally powered, electrically controlled prostheses have certain advantages over the cable-driven, body-powered prostheses, including superior pinch force (about 15–25 pounds as compared with 7–8 pounds); improved cosmetic and social acceptance; freedom from an uncomfortable harness; and improved function for high-level amputees. However, proponents of the more traditional cable-driven, body-powered prostheses claim that the cable-driven, body-powered prostheses are more functional and efficient because the reaction time to response is immediate, noise level is held to a minimum, and operation is more dependable and stable.

The conventional prostheses do not satisfy many of the basic needs of individuals who have either lost a limb or were born without a limb. In particular, there is a need for prosthetic devices that are lighter in weight, capable of operating all day (more than 12 hours) on a single charge, and provide the ability to drive an automobile without modification to the vehicle. Further, there is a desire for prosthetic devices which provide more function than existing devices, improved suspension and actuation, and improved gripping capabilities.

A tendon-activated, pneumatic controlled artificial hand having up to three independently functioning fingers has been developed. However, this device can only be used by individuals having a forearm and some phantom feeling (i.e., the sense that they can still feel their missing hand). It is believed that when this device is perfected, its users will be able to operate the artificial hand using muscles and muscle signals from the forearm. A computer will receive muscle signals from the forearm and transmit corresponding signals to the artificial hand to stimulate movement of the fingers.

A prosthetic limb has been developed that uses myoelectric signals to control a two-motor system. One motor operates to provide high torque at low speed, while a second motor provides low torque at high speed. Together, they accomplish reasonable torque and reasonable speed to provide simultaneous closure of the fingers against a fixed thumb, or simultaneous closure of the fingers and the thumb.

Another device uses a microprocessor to control grip force and finger/hand orientation of a prosthetic hand. This device uses two myoelectric inputs, including one for an extensor muscle, which when tensioned opens the hand wider, and one for a flexor muscle, which is used to switch the hand into a "hold" mode. The fingers curl continuously toward an opposed, moveable thumb. However, there is not any independent finger or wrist control.

A gloveless endoskeletal prosthetic hand has been developed having a multi-position passive thumb with four, three-jointed apposed fingers, which all move in unison. A harness cable control closes the fingers simultaneously, and the fingers extend upon relief of cable tension.

A prosthetic hand has been developed with co-contraction switching, where the wearer is able to switch control from the hand to the wrist by a quick twitch of the two control muscles. Control back to functions of the hand is restored by another quick twitch.

It is believed that there remains a need for a practical control device for generating a plurality of independent signals for controlling a plurality of functions in a prosthetic hand having a plurality of independently controllable fingers.

SUMMARY OF THE INVENTION

The invention provides a practical control device having up to eight independent channels of communication for simultaneously operating a plurality of electromechanical devices, or for simultaneously performing a plurality of independent functions on an electromechanical device, such as a prosthetic hand.

In accordance with an aspect of the invention, the controller includes a substrate having mounted thereon up to eight independently actuatable pressure sensors, and an integrated circuit board which includes a microcontroller and a microradio transmitter for converting pressure exerted on the sensors by various parts of a foot into control signals that are broadcast to a receiver and transmitted to an electromechanical device, such as a prosthetic hand, for operation thereof.

In a particular embodiment, the foot-operated controller of this invention comprises a substrate having a plurality of pressure sensors mounted at selected locations on the substrate to facilitate control of a controllable electromechanical device by application of pressure from selected parts of a foot to the sensors, a microprocessor for receiving input from the sensors and converting the sensor inputs into commands for the controllable electromechanical device, and a radio transmitter for telecommunicating the commands to a radio receiver in electrical communication with the controllable electromechanical device. The substrate is located on or within the insole of a shoe.

In a less refined aspect, the microprocessor may be hard-wired to the controllable electromechanical device, eliminating the need for a radio transmitter. In such case, the microprocessor may be located either in the shoe (e.g., on the substrate), or in/on the controllable electromechanical device.

In addition to having utility as a foot-operated controller for a prosthetic hand, the invention is also useful for controlling various other devices, such as robotic devices (e.g., a "third" hand), and power-assisted gloves or other exoskeletal devices, such as to aid stroke victims and others to manipulate their hand(s).

The device can also be used for discreetly generating and transmitting signals. This would, for example, allow a bank teller to secretly communicate with police or security personnel.

Another application of the device is in evaluating foot dexterity, e.g., to quantify the foot dexterity of an individual.

These and other features, advantages and objects of the present invention will be further understood and appreciated by those skilled in the art by reference to the following specification, claims and appended drawings.

DESCRIPTION OF THE PREFERRED EMBODIMENTS

Figure 1:
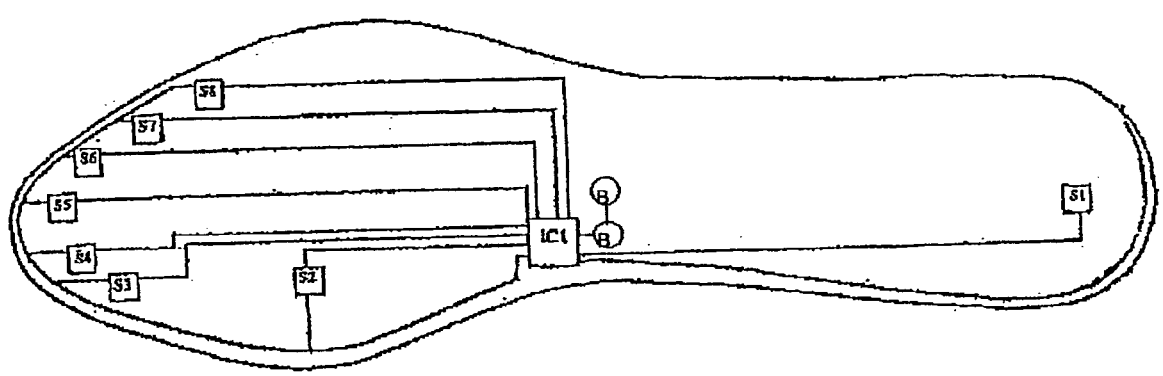
FIG. 1 is a schematic top view of a foot-operated controller in accordance with the invention.

There are located in a shoe insole insert, eight pressure sensors. FIG. 1, depicts the layout of the shoe insole insert.

The shoe insole insert constitutes a foot-operated controller that includes two miniature lithium batteries (B); an integrated circuit (IC) board, which includes a microcontroller and a microradio transmitter; and, eight pressure sensors (S1 through S8). The correspondence of the sensor locations to the movements of the wrist and hand, in the hand prosthesis application, are as follows:

| Location | Foot | Hand |
| --- | --- | --- |
| S1 | Heel | Wrist flexion/extension |
| S2 | Ball | Wrist pronation/supination |
| S3 | Inside of great toe | Thumb inversion/eversion |
| S4 | Great toe | Thumb flexion/extension |
| S5 | Second toe | Second finger flexion/extension |
| S6 | Third toe | Third finger flexion/extension |
| S7 | Fourth toe | Fourth finger flexion/extension |
| S8 | Fifth toe | Fifth finger flexion/extension |

The number, eight, is significant in that miniature electronic elements are packaged in powers of two; namely 2, 4, 8, 16, etc . . . . Eight channels of communication represent an optimal configuration. Although, in this foot control system, any number of activated channels less than eight is possible. More than eight channels of communication are also possible. However, it becomes increasingly difficult to develop adequate foot dexterity to control additional functions beyond eight.

Suitable pressure sensors are well known and used in many electronic devices, which have touch activation surfaces. They are approximately one centimeter in diameter, wafer-thin carbon-based resistors. The sensors change resistance with applied pressure, which is linear and inversely proportional to the pressure applied. These eight independent signals feed into a low-power microcontroller, located in the insole insert, as eight analog inputs. The microcontroller digitizes the eight signals into a command string, which is sent to a microradio transmitter, also located in the insole insert. The device may be powered by two miniature lithium batteries (B), which could provide a service life of about one month under continuous activation conditions.

Suitable microradio transmitters/receivers are well known and used in many hobby and commercial applications. These devices are sold in matched pairs, to ensure the exactness of frequency transmission and reception.

Once the signal is received, the receiver microcontroller has the capability to control any type of electrical device, since the software programming is written into the receiver. There can be numerous applications. The shoe insole insert controller may be used to operate a prosthetic hand utilizing pulse width modulation servomotors, such as those found in remote control airplane wing trim activators. Alternatively, the prosthetic hand may utilize linear induction motors. This customizability is one of the unique characteristics of the system.

Each microradio transmitter has its matched microradio receiver located in the prosthetic hand. A command string is received and sent to a low-power microcontroller, which decodes the digitized signal into eight independent commands for the hand. Since these command strings are being sent and received on the order of 400,000 times per second, the hand movement appears continuous. (There is a 4 megahertz crystal clock, controlling timing in the integrated circuit, which takes ten unique readings each command string cycle.)

The foot microcontoller is always on, when batteries are inserted. It operates in a sleep mode, and only powers up when a foot pressure sensor is activated. The sleep mode technology is currently used with desktop computers, which go into such a mode when not in use.

The controller may be powered by commercially available batteries, such as with CR2032 lithium batteries, which are commonly used for calculator and wristwatch applications. An extended battery life is possible because the electronics are only activated when they need to be sending or receiving signals, much like the operation of a television remote control.

Figure 3:
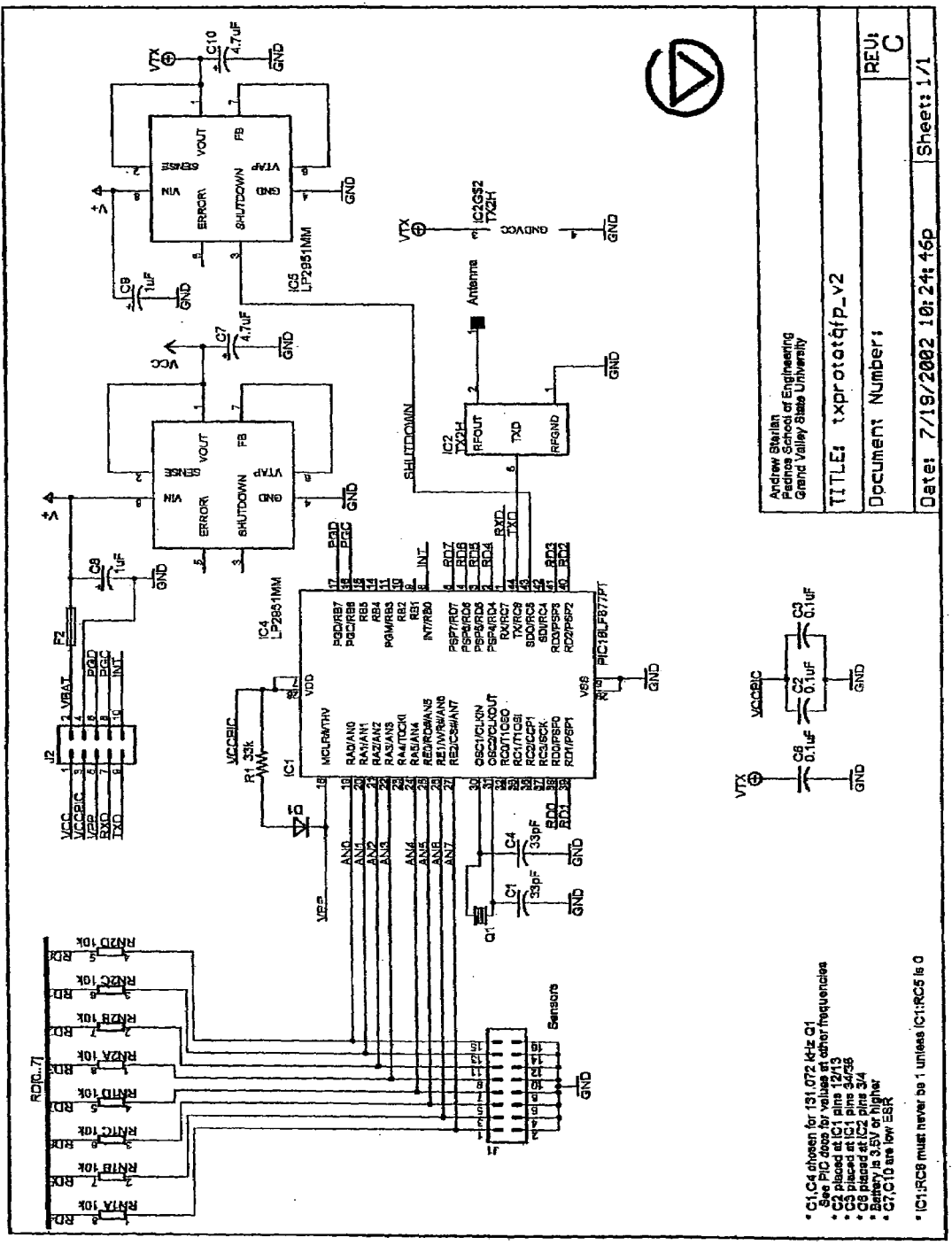
FIG. 3 is schematic of the integrated circuit board shown in FIG. 2.
Figure 4:
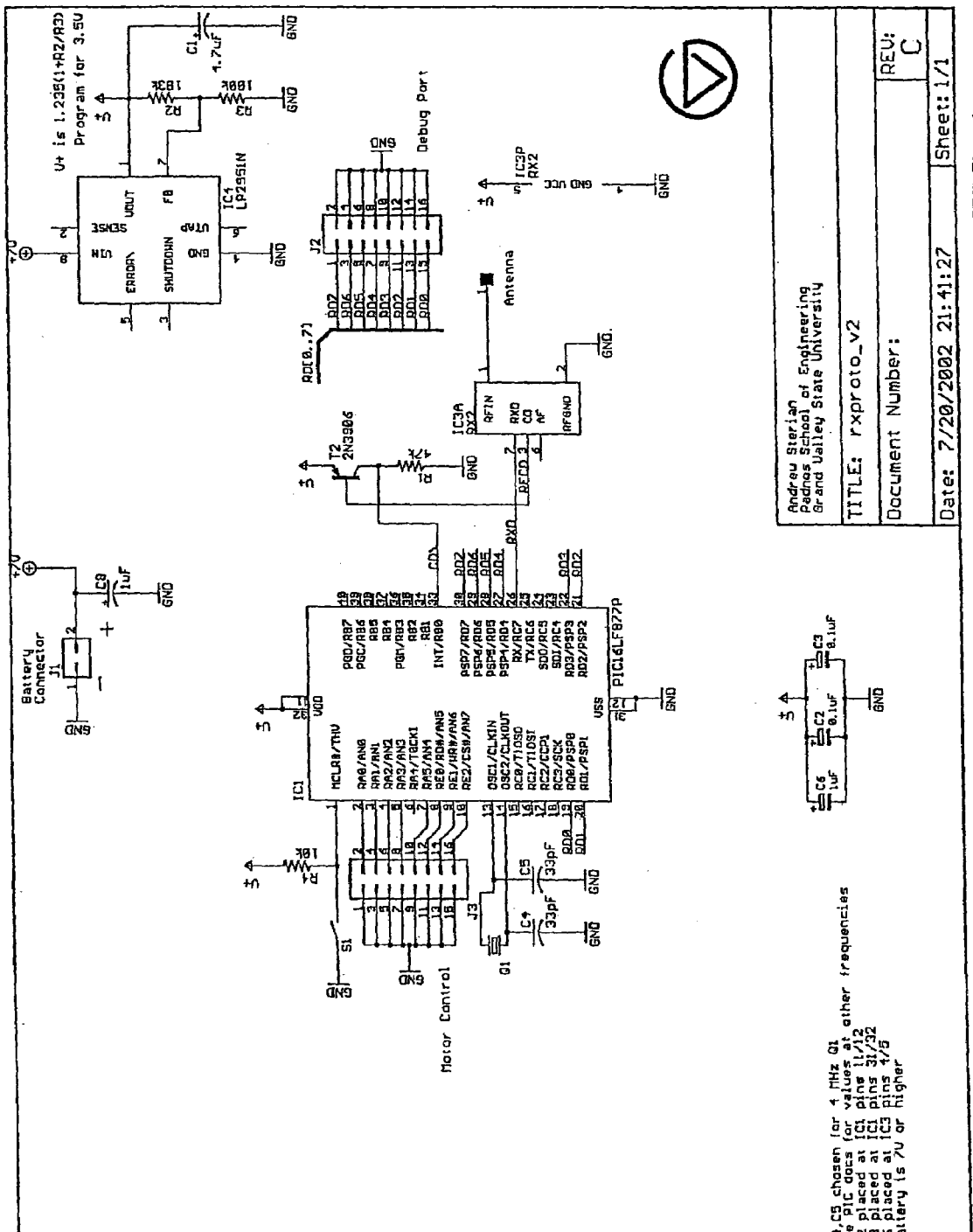
FIG. 4 is a schematic of an integrated circuit board for a receiver capable of receiving a signal from the microradio transmitter of the foot-operated controller of this invention.

A schematic of the integrated circuit board for the transmitter portion of the wireless communication link is shown in FIG. 3. A schematic of the integrated circuit board for the receiver portion is shown in FIG. 4.

The voltage is regulated to 3.0 volts by two voltage regulators to service two separate circuits. One circuit is dedicated to the foot microcontroller; and, the second is dedicated to the foot microradio transmitter. The microradio transmitter is only activated when the foot microcontroller has a sensor signal to send.

The sensors are Force Sensitive Resistors (FSR). They exhibit a decrease in resistance with an increase in applied force. Their specifications state that they operate over a temperature range of −30 C to 170 C, and are not sensitive to vibration, electromagnetic interference (EMI), or moisture. With an applied voltage, the sensors provide an analog signal to the foot microcontroller.

Suitable PIC (Programmable Integrated Circuit) microcontrollers are well known and currently utilized in many programmable electronic devices. The microcontroller operates with three areas of programming. One area is the base program, permanently in the chip, which operates in the background to control all the inputs, outputs, and communications between the other program areas. A second area, also permanently in the chip, is the special program instruction set, which interprets the programming steps of the third area. A third area is the set of commands, which are written in a PIC language by the application developer, and are programmed into the chip. This allows for the unique commands of the microcontroller in a given application.

The foot microcontroller converts the analog signal to a digital signal, by taking the maximum three volt analog signal and stepping it into ten 0.3 volt increments. This allows for ten discrete digital increments of any pressure sensor analog signal from the foot pressure sensors. The hand microcontroller reverses this process by taking the digital increment and reconverting it to a pulse width modulation signal, or other control signal, to operate any motorized devices.

The foot microcontroller assembles a command string, which is sent to the microradio transmitter for wireless communication to the receiver, where the microradio receiver gets it, and the hand microcontroller decodes it. The command string begins with a "junk" word; then, two zero bits; then, a security code, matched in the transmitter and receiver, to prevent errant radio signals, from interfering; then, eight sensor signals. If there is no match with the security code, the receiver goes back to sleep mode. The junk word takes the receiver out of the sleep mode. It acts like an alarm clock. The zero bits "wake up" the microcontroller, and set the timing of the remainder of the string. The security code ensures a match. Eight independent control signals follow. This is repeated at the rate of 400,000 cycles per second.

A suitable commercially available microradio transmitter is a Radiometrix TX2 transmitter, with matched receiver, that is FCC approved for this type of wireless communication. (The transmitter is UL-approved and complies with FCC Part 15 regulations.) The effective radiated power is governed by the few inches of antenna length. The effective signal range is limited to a few meters. The effective radiated power from the transmitter is significantly less than that emitted by a cellular telephone.

Figure 2:
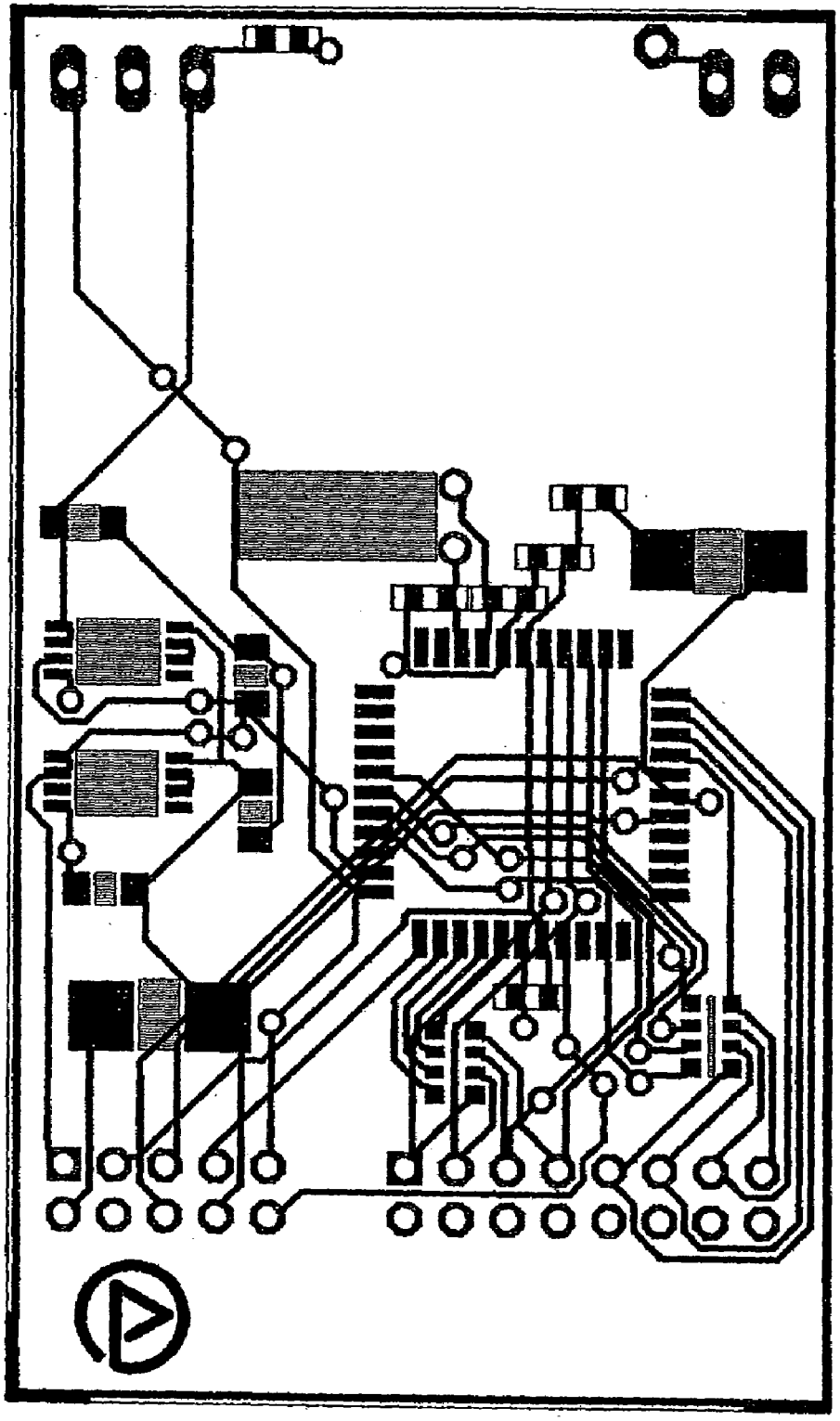
FIG. 2 is a top plan view of an integrated circuit board including a microcontroller and microradio transmitter suitable for use in the foot-operated controller of the invention.

All of the electronic components, which comprise the integrated circuit of the shoe insole insert are mounted on a circuit board, which is shown in FIG. 2. Further miniaturization to reduce the board size is possible.

The integrated circuit board contains the major components of the microcontroller and the microradio transmitter. The board may be layered within a laminated construction of the shoe insole insert.

The foot microcontroller sends a signal to the microradio transmitter to first turn it on; and then sends the command string signal to the frequency-matched microradio receiver in the prosthetic hand. When not active, the hand microcontroller stays in a sleep mode. The hand microcontroller remembers and holds the last signal sent. This allows the wearer of a prosthetic hand, for example, to turn off the hand electronics, by way of a myoelectric inhibitor, hold the hand's position, and move about on the foot without concern of the hand reverting to a normally open or a normally closed position. Using a myoelectric impulse for this function allows activation and deactivation of the device to occur virtually unnoticed.

The above description is considered that of the preferred embodiments only. Modifications of the invention will occur to those skilled in the art and to those who make or use the invention. Therefore, it is understood that the embodiment shown in the drawings and described above are merely for illustrative purposes and not intended to limit the scope of the invention, which is defined by the following claims as interpreted according to the principles of patent law, including the doctrine of equivalents.

The invention claimed is:

1. A prosthetic system comprising:
   a controllable prosthetic device;
   a shoe insole insert including a substrate having a plurality of pressure sensors mounted at selected locations on the substrate to facilitate control of the controllable prosthetic device by application of pressure from selected parts of a foot to the sensors; and
   a microprocessor for receiving input from the sensors and converting the sensor inputs into commands for the controllable prosthetic device.

2. The prosthetic system of claim 1, wherein the prosthetic device is a prosthetic hand.

3. The prosthetic system of claim 1, further comprising a radio transmitter for sending the commands to the controllable prosthetic device.

4. The prosthetic system of claim 1, located on or within a shoe.

5. The prosthetic system of claim 1, in which the microprocessor is hard-wired to the controllable device.

6. The prosthetic system of claim 1, wherein the microprocessor is located on the substrate.

7. The foot-operated controller of claim 1 further comprising a controllable prosthetic device operatively connected to the microprocessor to provide commands to the controllable prosthetic device in response to input from the sensors of the foot-operated controller.

* * * * *